US008500672B2

(12) United States Patent
Caleffi et al.

(10) Patent No.: US 8,500,672 B2
(45) Date of Patent: Aug. 6, 2013

(54) EXTRACORPOREAL BLOOD CIRCUIT

(75) Inventors: Luca Caleffi, Carpi (IT); Giuseppe Franzoni, Sassuolo (IT); Francesco Ribolzi, Varese (IT); Ranko Sakota, Giugliano in Campania (IT); Antonio Rega, Salerno (IT); Aldo Calimeri, Mirandola (IT); Davide Marchesi, Modena (IT)

(73) Assignee: Gambro Lundia AB, Lund (SE)

( * ) Notice: Subject to any disclaimer, the term of this patent is extended or adjusted under 35 U.S.C. 154(b) by 296 days.

(21) Appl. No.: 12/745,454

(22) PCT Filed: Dec. 4, 2007

(86) PCT No.: PCT/IB2007/003744
§ 371 (c)(1),
(2), (4) Date: Jun. 14, 2010

(87) PCT Pub. No.: WO2009/071961
PCT Pub. Date: Jun. 11, 2009

(65) Prior Publication Data
US 2010/0274171 A1 Oct. 28, 2010

(51) Int. Cl.
*A61M 37/00* (2006.01)
(52) U.S. Cl.
USPC ........................................................ 604/6.09
(58) Field of Classification Search
USPC ........................................................ 604/6.09
See application file for complete search history.

(56) References Cited

U.S. PATENT DOCUMENTS

| 4,052,315 | A | * | 10/1977 | Lindsay et al. | 210/232 |
|---|---|---|---|---|---|
| 4,666,598 | A | * | 5/1987 | Heath et al. | 210/239 |
| 4,676,771 | A | | 6/1987 | Henke | |
| 4,770,787 | A | * | 9/1988 | Heath et al. | 210/646 |
| 5,328,461 | A | * | 7/1994 | Utterberg | 604/80 |
| 5,330,425 | A | * | 7/1994 | Utterberg | 604/83 |
| 5,489,385 | A | * | 2/1996 | Raabe et al. | 210/448 |
| 5,503,801 | A | | 4/1996 | Brugger | |
| 5,545,318 | A | * | 8/1996 | Richmond | 210/232 |
| 5,591,251 | A | * | 1/1997 | Brugger | 95/242 |
| 5,674,199 | A | | 10/1997 | Brugger | |
| 5,895,578 | A | * | 4/1999 | Simard et al. | 210/636 |
| 5,941,842 | A | * | 8/1999 | Steele et al. | 604/4.01 |
| 6,187,198 | B1 | * | 2/2001 | Utterberg | 210/645 |
| 6,464,878 | B2 | * | 10/2002 | Utterberg | 210/645 |
| 6,468,427 | B1 | | 10/2002 | Frey | |
| 6,949,214 | B2 | * | 9/2005 | Frey | 264/328.1 |

(Continued)

FOREIGN PATENT DOCUMENTS
DE  31 43 456 A1  5/1983
JP  7 299136 A  11/1995
(Continued)

*Primary Examiner* — Leslie Deak
*Assistant Examiner* — Guy K Townsend
(74) *Attorney, Agent, or Firm* — Pearne & Gordon LLP

(57) ABSTRACT

An extracorporeal blood circuit, comprising an expansion chamber for air-blood separation, wherein a filter (38) retains the solid particles in the blood. The filter has a trunco-conical filtering wall with a vertical axis surmounted by a top head (43) provided with upper openings (44) conformed and arranged such as to define a fluid passage which is asymmetrical with respect to the vertical axis. The top head does not retain air bubbles internally thereof, thus preventing a situation in which the air bubbles are directed towards an outlet of the expansion chamber and thus towards the patient. The extracorporeal circuit is used in a dialysis apparatus.

36 Claims, 11 Drawing Sheets

U.S. PATENT DOCUMENTS

| | | | |
|---|---|---|---|
| 2003/0006187 A1 | 1/2003 | Frey | |
| 2003/0138348 A1* | 7/2003 | Bell et al. | 422/44 |
| 2004/0186416 A1* | 9/2004 | Caleffi | 604/6.16 |
| 2004/0219059 A1* | 11/2004 | Barringer et al. | 422/44 |
| 2005/0063860 A1* | 3/2005 | Carpenter et al. | 422/45 |
| 2010/0256547 A1* | 10/2010 | Ribolzi et al. | 604/7 |

FOREIGN PATENT DOCUMENTS

| | | |
|---|---|---|
| JP | 9 140788 A | 6/1997 |
| WO | 00/18482 A1 | 4/2000 |
| WO | 2008/065472 A1 | 6/2008 |

* cited by examiner

EXTRACORPOREAL BLOOD CIRCUIT

BACKGROUND OF THE INVENTION

The invention relates to an extracorporeal blood circuit, in particular an extracorporeal blood circuit provided with an expansion chamber with a blood filter designed for retaining small bodies (for example blood clots) contained in the blood flow.

Specifically, though not exclusively, the invention can be usefully applied in a blood return line (venous line) of the extracorporeal blood circuit used in a dialysis or hemo(dia) filtration treatment, or another extracorporeal blood treatment which might require the use of an extracorporeal blood circuit.

JP 7299136 describes an expansion chamber for a blood circuit having on a bottom thereof a truncoconical filter having a lower opening which communicates with a blood outlet port. The chamber is superiorly closed by a cover which also exhibits a hole for enabling passage of a tube for inlet of the blood into the chamber.

JP 9140788 describes a blood chamber in which a filter has a tubular filter wall, superiorly closed by a head exhibiting holes, which holes are arranged symmetrically with respect to the axis of the tubular wall and are orientated with the external openings facing upwards.

U.S. Pat. No. 4,676,771 describes an arterial blood filter comprising an expansion chamber having a first port for blood inlet, a second port for blood outlet, a tubular body predisposed in the chamber for preventing passage of non-dissolved gases towards the outlet, and a top head having a fluid-impermeable wall which superiorly closes the tubular body.

DE 3143456 discloses an infusion device provided with a drip chamber internally bearing a holed tubular filtering wall having a top end which is obliquely cut and closed by a cover connected to an upwardly-projecting breather tube. The breather tube prevents the air from moving towards the patient, passing through the lower outlet of the drip chamber.

One of the drawbacks of the expansion chambers used in the extracorporeal blood circuits of known type is connected with the prevention of air bubbles and/or solid particles present in the blood flow passing through the chamber from being transported towards the patient's vascular circuit.

As mentioned above, the prior art includes use of a filter in the venous expansion chambers in order to retain solid particles. These venous filters, however, can retain and facilitate the collecting of air bubbles, especially (but not only) during the stage of priming the extracorporeal blood circuit, i.e. the stage which precedes the actual treatment, in which the extracorporeal blood circuit is emptied of air and filled with a priming fluid. If during this stage the venous filter retains an air bubble, there is the risk that during treatment, with the patient connected up to the extracorporeal circuit, the air bubble might detach from the venous filter and shift towards the patient.

SUMMARY OF THE INVENTION

An aim of the present invention is to provide a circuit having a blood chamber with a filter able to retain solid particles efficiently while at the same time not leading to collection of gas bubbles.

An advantage of the invention is to provide a blood chamber provided with a filter that is constructionally simple and economical.

A further advantage is to make available a blood circuit having a filter which can retain solid particles and not retain any air bubbles not dissolved in the liquid flowing in the circuit; any air bubbles can freely rise towards the upper part of the expansion chamber up until reaching a gas-liquid separation zone, e.g. the level of the liquid or a vent provided with a hydrophobic filter.

A still further advantage is that the invention gives rise to an extracorporeal blood circuit which avoids the risk of introducing solid particles or air bubbles into the patient connected to the circuit.

In a specific embodiment of the invention, the blood circuit comprises a gas-liquid separation chamber arranged on the venous line returning the blood to the patient, in which a filter configured for retaining the solid particulate contained in the blood flow has a top head which includes a fluid passage conformed asymmetrically with respect to a longitudinal axis of the filter.

These aims and others besides are all attained by the present invention, as it is characterised in one or more of the appended claims.

Further characteristics and advantages of the present invention will better emerge from the detailed description that follows, of at least an embodiment of the invention, illustrated by way of non-limiting example in the accompanying figures of the drawings.

BRIEF DESCRIPTION OF THE DRAWINGS

The description will be made herein below with reference to the accompanying figures of the drawings, provided by way of non-limiting example.

DETAILED DESCRIPTION

Figure 1:
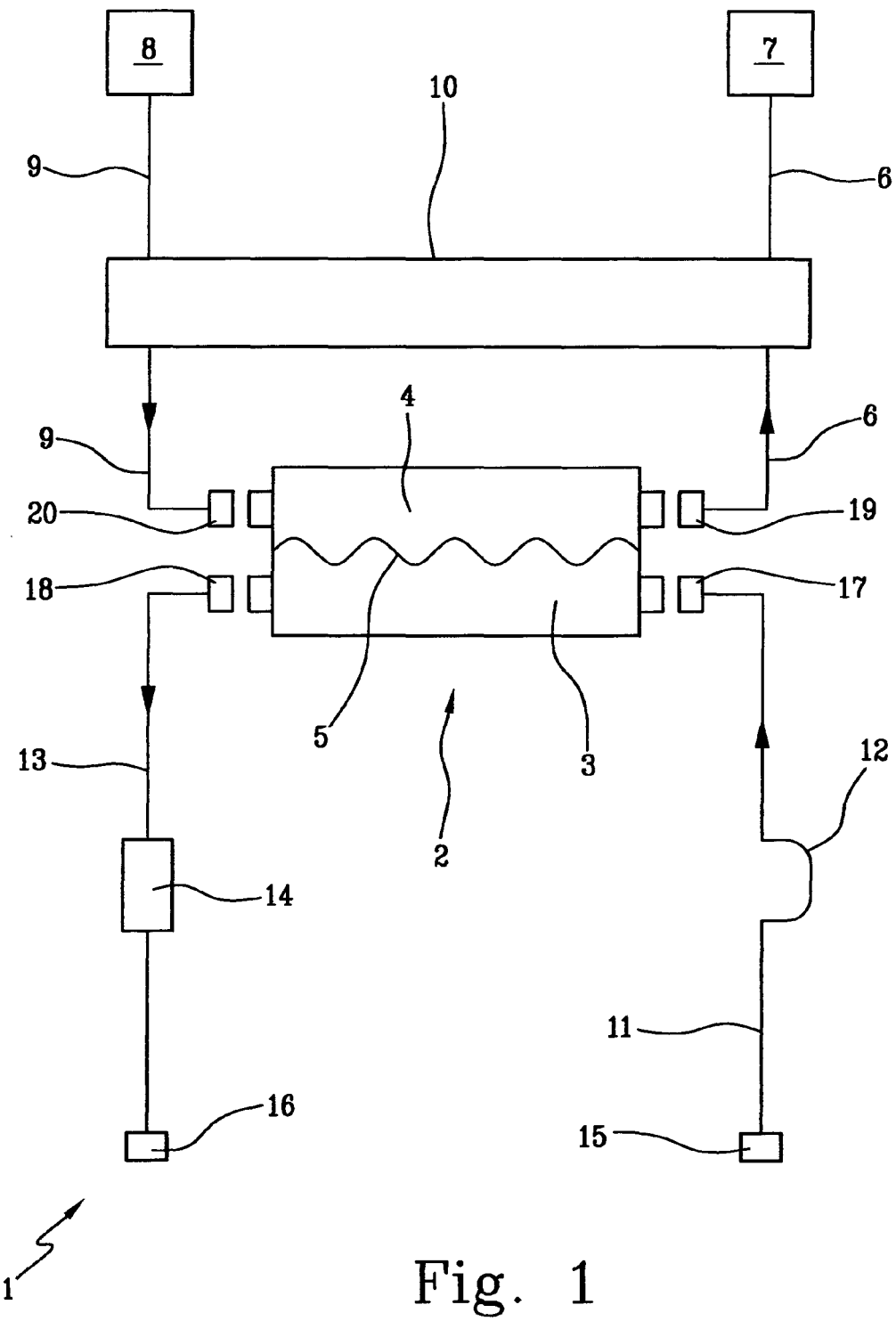
FIG. 1 is an extracorporeal blood treatment apparatus provided with an expansion chamber realised according to the invention.

With reference to FIG. 1, 1 denotes in its entirety an extracorporeal blood treatment apparatus. In the specific case the treatment apparatus 1 comprises a dialysis apparatus. The treatment apparatus 1 comprises a membrane device 2 having a blood chamber 3 and a fluid chamber 4 which are separated from one another by a semipermeable membrane 5. In the specific embodiment the membrane device 2 comprises a dialysis filter. The treatment apparatus 1 comprises a fluid circuit having a used fluid discharge line 6 which connects the fluid chamber 4 to a drainage 7. The used fluid discharge line 6 is provided with sensors and actuators, of known type and not illustrated, which are provided on the used fluid discharge line in any of the dialysis or hemo(dia)filtration apparatus of known type. The treatment apparatus 1 comprises at least a fresh fluid source 8. The source, in the example, comprises a dialysis fluid source. The source 8 can comprise an in-line preparation device of a treatment fluid (for example a dialysis fluid or a replacement fluid for a hemofiltration treatment) starting from water and concentrates, or it can comprise one or more batch containers of ready-to-use fluid, or it can comprise any source of treatment fluid used in any dialysis or hemo(dia)filtration apparatus of known type. The treatment apparatus 1 comprises at least a supply line of fresh fluid 9 which connects the fresh fluid source 8 to the fluid chamber 4. The fresh fluid supply line 9 is provided with sensors and actuators, of known type and not illustrated, which the fresh fluid supply line is provided with in any one of the dialysis or hemo(dia)filtration apparatus of known type. The treatment apparatus 1 comprises a fluid balance device 10, configured to control the patient's weight loss during the treatment. The fluid balance device 10 comprises any one of the known-type devices usable in a dialysis or hemo(dia)filtration apparatus, for example of the flow-meter type (mass or volumetric flow-meters, dual flow-meters providing dual signals proportional to dual flows or differential flow-meters providing signals proportional to flow differences), volumetric balance chambers, scales, etc. In a version of the treatment apparatus realised according to the invention and not illustrated, the treatment apparatus comprises a hemo(dia)filtration apparatus and the fresh fluid source is connected to the extracorporeal blood circuit, before and/or after the membrane device 2.

The treatment apparatus 1 further comprises an extracorporeal blood circuit connected to the blood chamber 3. The extracorporeal blood circuit comprises an arterial line 11, i.e. a blood transport line which takes the blood to be treated from the patient towards the membrane device 2. The arterial line 11 is provided with a pump tract 12 predisposed for coupling with a blood pump (for example a tube deformation pump) of known type and not illustrated. The extracorporeal blood circuit comprises a venous line 13, i.e. a blood transport line which returns the treated blood from the membrane device 2 to the patient. The venous line 13 is provided with an expansion chamber 14 in which, during use, the air which is not dissolved in the blood crossing the expansion chamber 14 is separated from the blood itself. In the specific embodiment, the separated air accumulates in the upper part of the expansion chamber 14, while the blood fills the lower part of the chamber itself, forming a liquid level which represents the gas-liquid separation zone. The expansion or separation chamber 14 defines a broadening of the fluid passage along the fluid transport line to enable separation of the non-dissolved gassy parts. The expansion chamber 14 will be described in greater detail herein below with reference to FIG. 3 and following. According to another embodiment not illustrated, the expansion chamber has a vent provided with a hydrophobic element preventing the passage of liquid; in this specific embodiment the expansion chamber may be configured to be, during use, completely full of liquid. According to a further embodiment, the extracorporeal blood circuit may have a plurality of expansion/separation chambers, e.g. the circuit may be configured to be a single needle circuit (e.g. circuit of single/double pump type and of the type provided with one or more arterial expansion/separation chambers and one or more venous expansion/separation chambers).

One of the aspects of the invention is, particularly, the configuration of the filter for solid particles operatively associated to the expansion or separation chamber. The configuration can relate particularly to the conformation of the filter and/or the relative arrangement thereof with respect to the expansion chamber. The filter will be described in detail herein below, with reference to a special expansion chamber, but it can be applied and operatively associated to any expansion chamber of known type used in an extracorporeal blood circuit for gas-liquid separation.

The arterial line 11 and the venous line 13 are each provided with a patient end 15 and 16, predisposed for removable connection to the patient via a vascular access device (of known type and not illustrated), and a device end 17 and 18 predisposed for removable connection via an access port (respectively the inlet and the outlet) to the blood chamber 3 of the membrane device 2. The used fluid discharge line 6 and the fresh fluid supply line 9 are each provided with a device end 19 and 20 predisposed for removable connection, via an access port (respectively an outlet and an inlet), to the fluid chamber 4 of the membrane device 2.

Figure 2:
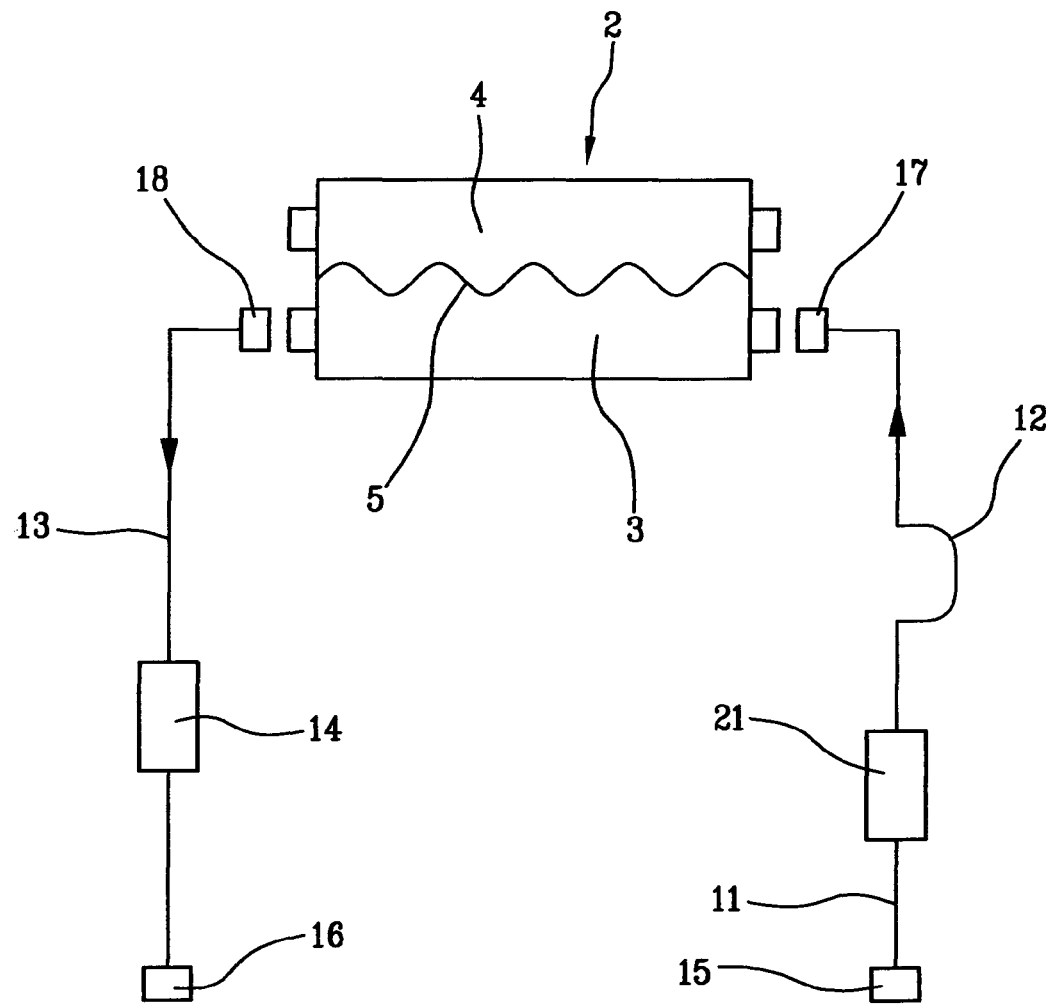
FIG. 2 is a partial view of a second embodiment of an extracorporeal blood apparatus provided with an expansion chamber realised according to the invention.

FIG. 2 illustrates an apparatus which is similar to the apparatus of FIG. 1 (the treatment fluid circuit has not been illustrated for reasons of simplicity), in which the arterial line 11 is provided with an expansion chamber 21 for separation of air from the blood. In the specific embodiment the arterial expansion chamber 21 is arranged between the patient end 15 and the pump tract 12.

Figure 3:
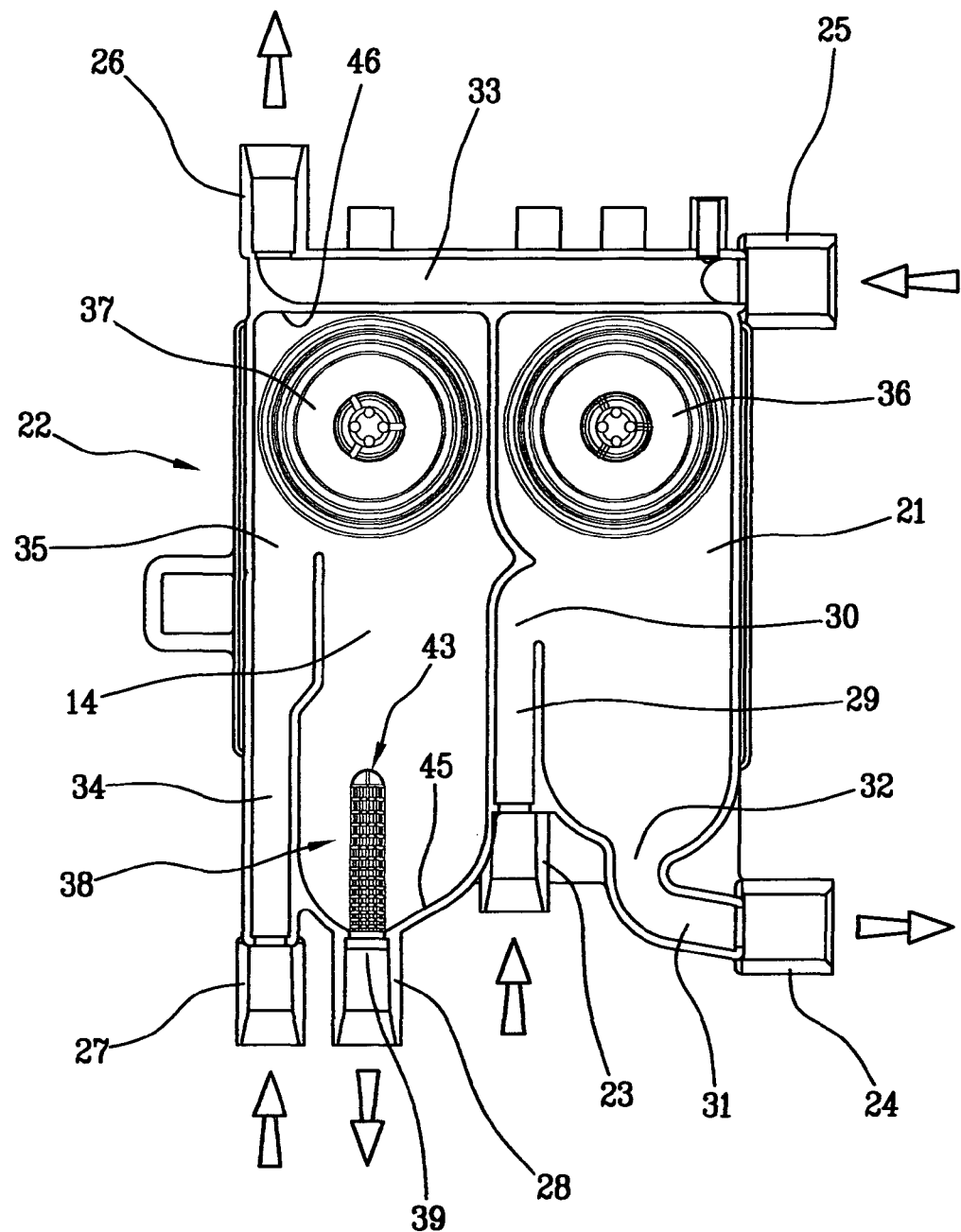
FIG. 3 is a cassette device comprising an expansion chamber realised according to the invention.
Figure 4:
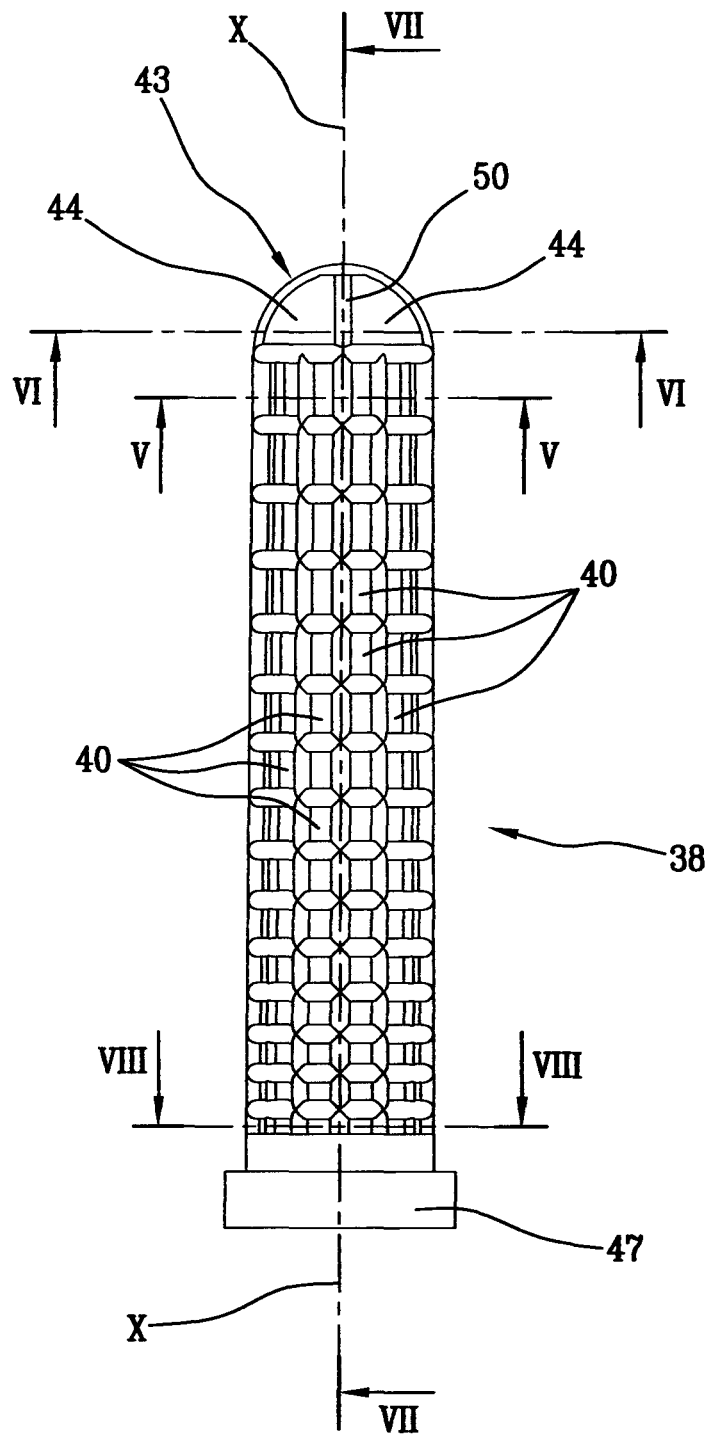
FIG. 4 is an enlarged-scale illustration of a lateral view from the left of filter 38 of FIG. 3.

FIG. 3 illustrates a cassette device 22 inserted in an extracorporeal blood circuit which is functionally the same as that of the apparatus of FIG. 2. The cassette device 22 integrates, in a single block, the venous expansion chamber 14 and the arterial expansion chamber 21. The cassette device 22 comprises: a first tubular connection 23 for the blood inlet of the arterial chamber 21 and for connection of an outlet end of an initial tract of arterial line 11 (i.e. an initial tract which goes from the patient end 15 to the outlet end); a second tubular connection 24 for the blood outlet from the arterial chamber 21 and for the connection of the aspiration or inlet end of the pump tract 12 (of known type and not illustrated in FIG. 3 for reasons of simplicity); a third tubular connection 25 for the connection of the delivery or outlet end of the pump tract 12; a fourth tubular connection 26 for connection of an inlet end of a final tract of arterial line 11 (i.e. a final tract going from the inlet end to the device end 17); a fifth tubular connection 27 for the connection of an outlet end of an initial tract of venous line 13 (i.e. an initial tract which goes from the device end 18 to the outlet end); a sixth tubular connection 28 for connection of an inlet end of a final tract of venous line 13 (i.e. a final tract going from the inlet end to the patient end 16).

In FIG. 3, for the sake of clarity, the direction of the blood flow during the extracorporeal treatment has been indicated by a series of arrows.

The initial tract of the venous line 13 of blood transport has an end (device end 18) designed for connection with the membrane device 2. The final tract of the venous line 13 for blood transport has an end (patient end 16) designed for connection with an access device to the vascular system of a patient.

The cassette device further comprises: a first conduit 29 for connecting the first tubular connection 23 with an inlet port 30 of the arterial expansion chamber 21; a second conduit 31 for connecting an outlet port 32 of the arterial expansion chamber 21 with the second tubular connection 24; a third conduit 33 for connecting the third tubular connection 25 with the fourth tubular connection 26; a fourth conduit 34 for connecting the fifth tubular connection 27 with an inlet port 35 of the venous expansion chamber 14. The arterial expansion chamber 21 is provided with a pressure sensor 36. The venous expansion chamber 14 is provided with a pressure sensor 37. Each pressure sensor 36 and 37 may be of the membrane type which is impermeable to fluids, having a side facing towards the inside of the respective chamber and the opposite side destined to be connected with an external pressure transducer (of known type and not illustrated).

The arterial blood transport line 11 may comprise at least a tract of flexible tube designed for blood transport. The venous blood transport line 13 may comprise at least a tract of flexible tube designed for blood transport. In the specific embodiment the above-mentioned initial tract of arterial line 11, the above-mentioned final tract of arterial line 11, the above-mentioned initial tract of venous line 13 and the above-mentioned final tract of venous line 13 comprise a tract of flexible tube configured for blood transport.

The venous expansion chamber 14 is internally provided with a filter 38 arranged at an outlet port 39 of the chamber 14. The filter 38 serves to retain small bodies contained in the blood flow (for example small coagulated blood clots in the membrane device 2 or in other parts of the extracorporeal circuit) to prevent the entry thereof into the cardiovascular system of the patient. The filter 38 is described with reference to the venous expansion chamber 14 of the cassette device of FIG. 3, though the filter 38 might be used in an expansion chamber which is not part of a cassette device (for example the expansion chamber 14 of the apparatus of FIG. 1 or FIG. 2, or any other gas-liquid separation chamber used in an extracorporeal blood circuit). The filter 38 will be described in greater detail in figures from 4 onwards.

The filter 38 comprises a tubular filtering wall configured for retaining solid corpuscles in the blood flow moving from the first blood inlet port 35 to the second blood inlet port 39. The tubular filtering wall is provided with a plurality of lateral openings 40 that allow passage of non-dissolved gases in the blood flow. The tubular filtering wall comprises a tubular net realised in a single piece by plastic moulding. Each hole (mesh) of the tubular net forms a lateral opening 40. The tubular filtering wall has a longitudinal axis x-x. The longitudinal axis x-x of the tubular filtering wall extends at least in part vertically (non-horizontally), with reference to a use configuration of the expansion chamber 14. In the specific embodiment the longitudinal axis x-x of the tubular filtering wall extends vertically, with reference to a use configuration of the expansion chamber 14. The longitudinal axis x-x of the tubular filtering wall may be at lest partially oblique. The longitudinal axis x-x of the tubular filtering wall may be coaxial with an axis of the second blood outlet port 39.

The lateral openings 40 are configured such as to offer a greater resistance to the blood flow in the lower part of the tubular filtering wall and a smaller resistance in the upper part of the tubular filtering wall. In particular, the lateral openings 40 are smaller (that is, they have smaller fluid passage section) in the lower part and are larger in the upper part. In the specific embodiment the size of the lateral openings 40 grows gradually going from bottom to top, still with reference to the use configuration of the expansion chamber 14. The total size of the lateral openings 40 (i.e. the sum of the sizes thereof) is greater than the size of the second blood outlet port 39, e.g. 2 to 12 times as great as port 39, or 6 to 10 times as great as port 39, or about 8 times as great as port 39.

The tubular filtering wall has a lower end 41 which is open and which communicates with the second blood outlet port 39. The tubular filtering wall has an upper end 42 which extends on a lie plane which is perpendicular to the longitudinal axis x-x.

The filter 38 comprises a top head 43 inferiorly delimited by the upper end 42 of the tubular filtering wall. The top head 43 is provided with one or more upper openings 44. The upper openings 44 are oriented in a oblique direction with respect to the longitudinal axis x-x. The above-mentioned upper openings 44 form a passage for non-dissolved gas conformed and/or arranged asymmetrically with respect to the longitudinal axis x-x of the tubular filtering wall. It has been found that the asymmetrical arrangement of the upper openings 44, i.e. the openings arranged in the top head 43 of the filter 38, may facilitate detachment of any air bubbles from the surface of the filter, such as to prevent air bubbles being retained and reducing the risk that bubbles might be directed, dangerously, towards the outlet 39 of the expansion/separation chamber. Substantially, the asymmetrical conformation of the fluid passage of the top head of the filter can reduce the possibility of an air-bubble retention situation where the bubbles adhere to the filter surface 38. This situation could obtain, in particular, during the priming procedure of the extracorporeal circuit, especially (but not only) if the priming procedure includes stages in which the flow of the priming fluid is directed towards the outside of the tubular filtering wall of the filter 38 (i.e. in the opposite direction to the normal blood flow direction during the treatment) or during a phase of filling the chamber with priming fluid.

The tubular filtering wall has a tapered shape with the reduction thereof (gradual or discrete) of the transversal section going from the bottom first end 41 to the upper second end 42 (i.e. upwards with reference to the use configuration of the expansion/separation chamber). In the specific embodiment the tubular filtering wall has a truncoconical external surface (with slight concinnity) which is coaxial to the longitudinal axis x-x. The tubular filtering wall can alternatively have a cylindrical shape which is coaxial to the longitudinal axis x-x. The tubular filtering wall can, more generally, have an external surface which is axialsymmetric about the above-cited longitudinal axis x-x. The upper end 42 of the tubular filtering wall has a smaller diameter than a diameter of the second blood outlet port 39; in this way, during a stage of assembly of the extracorporeal blood circuit, the filter 38 can be easily inserted internally of the expansion chamber 14 passing through the second blood outlet port 39. According to another embodiment, the upper end 42 of the tubular filtering wall may have the same or greater diameter than a diameter of the second blood outlet port 39 and may be elastically deformable so as to be insertable internally of the expansion chamber 14 passing through the port 39.

The top head 43 has an external surface which is asymmetrically shaped with respect to the above-cited longitudinal axis x-x. In the specific case the external surface of the top head 43 is, for about half its extension, dome-shaped, or spherically shaped, and for the other half of its extension it is substantially open or at most provided with one or more ribs which define two or more relatively large fluid passage openings (larger than the lateral openings 40) in order to facilitate the detachment of the air bubbles.

The expansion chamber 14 has a bottom 45 and a top 46. The second blood outlet port 39 is arranged on the bottom 45. The bottom 45 is inclined towards the outlet 39. The first blood inlet port 35 is arranged between the bottom 45 and the top 46. The tubular filtering wall of the filter 38 extends longitudinally between the bottom 45 and the top 46. The lower end 41 of the tubular filtering wall is solidly connected to the bottom 45 of the expansion chamber 14. In particular, the filter 38 comprises a base 47 which is solidly connected to the bottom 45 of the expansion chamber 14. The base 47 is collar-shaped, having a greater diameter than the diameter of the second blood outlet port 39. The collar is engaged (by joint and/or by forcing and/or by gluing and/or by welding) to the second blood outlet port 39 and/or to the sixth tubular connection 28.

Each of the upper openings 44 is arranged closer to the bottom 45 than to the top 46. Each upper opening 44 is arranged at a distance from the top 46 which is at least double (in the specific case more than triple) the distance thereof from the bottom 45. At least one (in the specific case each) of the upper openings 44 is arranged closer to the bottom 45 than to the first blood inlet port 35. At least one (in the specific case each) of the upper openings 44 is arranged at a distance from the first blood inlet port 35, which is at least one and a half times the distance from the bottom 45. Each of these special relative arrangements of the upper openings 44 enables relatively large upper openings 44 to be realised (larger than the lateral openings 40, in particular larger than the mean size of the lateral openings 40, but also larger than the largest-size lateral openings 40, i.e. the highest-positioned lateral openings), and at the same time enable effective retention of solid particles (blood clots and others) contained in the blood flow.

The special arrangement of the filter 38 means that the path of the solid particles, especially the largest particles, never interests nor passes close to the top head 43, but in the worst scenario interests or passes close to the lateral openings 40, especially those arranged in the lower part of the tubular filtering wall which are, as mentioned, the smallest lateral openings 40. Apart from the arrangement of the top head 43 in a zone of the expansion chamber not interested by the passage of large solid particles, there may be another factor that further reduces the risk of not retaining the particles: this factor is represented by the special disposition of the upper openings 44 on the top head 43, as will be explained herein below.

At least a part of the top head 43 has a dome-shaped external surface. Each of the upper openings 44 is at least partially oriented in a transversal direction with respect to the above-cited longitudinal axis x-x.

The plurality of lateral openings 40 defines, overall, a mean passage section per opening, equal to the overall fluid passage section defined by the lateral openings 40 divided by the number of openings. At least one of the one or more upper openings 44 has a passage section which is larger than the mean passage section per opening. In particular each upper opening 44 has a passage section which is greater than the mean passage section per opening. Each upper opening 44 has a passage section which is at least double the above-cited means passage section per opening. Each upper opening 44 has a passage section which is greater than the passage section of any of the lateral openings 40. Each upper opening 44 is arranged at a lower level than the first blood inlet port 35, with reference to a use configuration of the expansion chamber (the configuration in which the plane of FIG. 3 is a vertical plane). The largest possible circle that can be drawn interior to each of the plurality of lateral openings 40 is smaller than the largest possible circle that can be drawn interior to each of the one or more upper openings 44.

The tubular filtering wall is realised in a single piece by plastic moulding. The tubular filtering wall of the filter 38 and the top head 43 are integrated in a single piece, made by plastic moulding.

Figure 5:
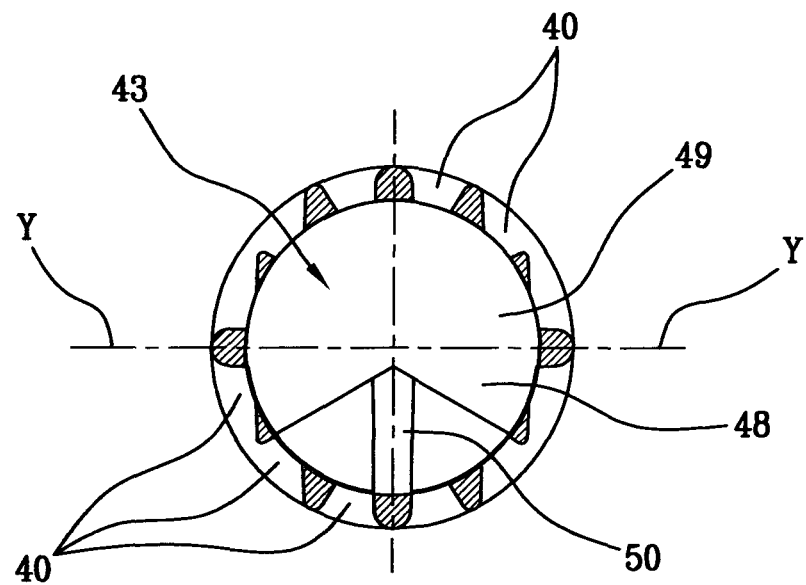
FIG. 5 is a section made according to plane V-V of FIG. 4.
Figure 6:
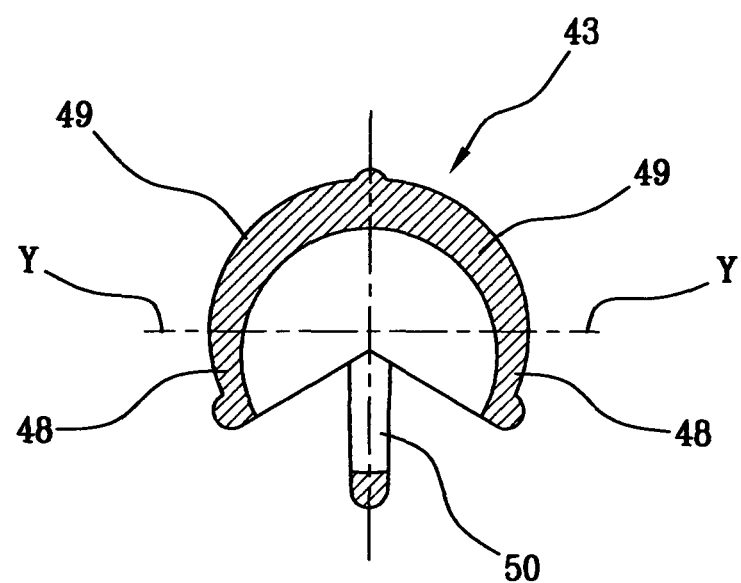
FIG. 6 is a section made according to plane VI-VI of FIG. 4.
Figure 7:
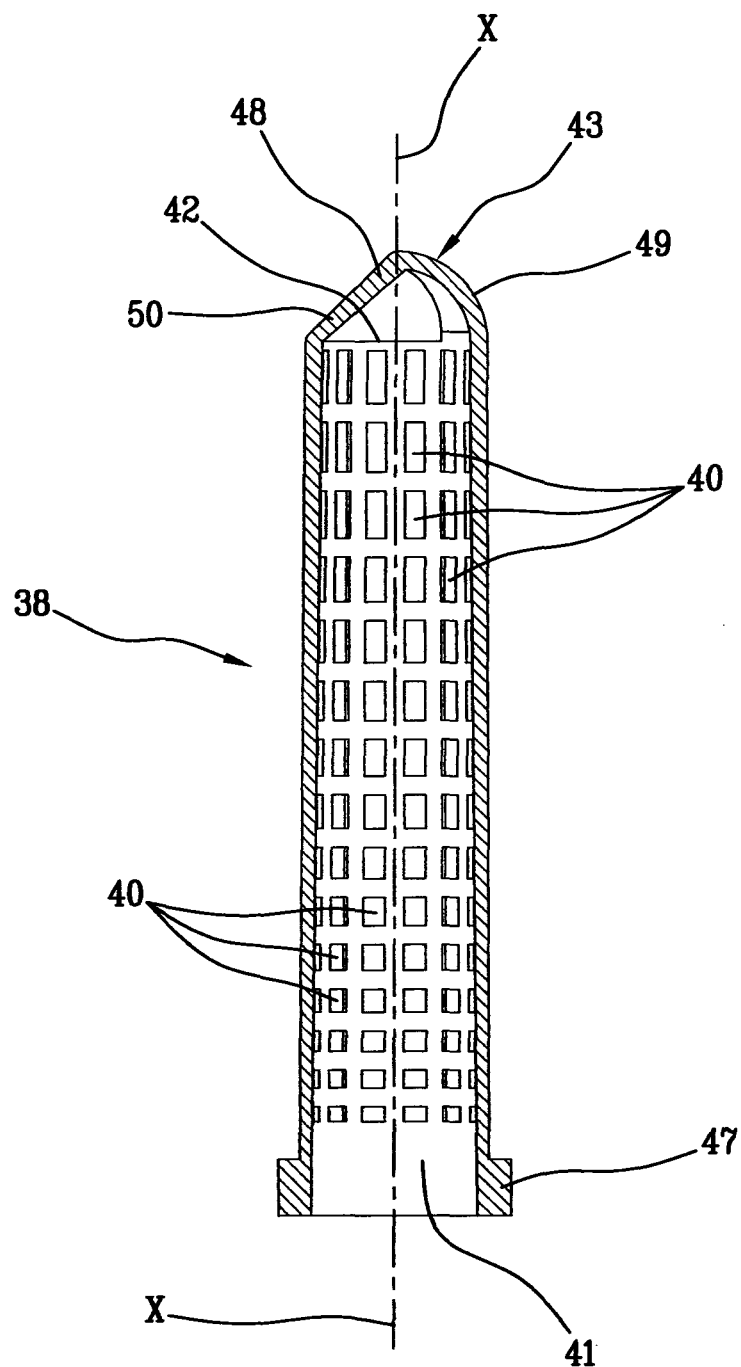
FIG. 7 is a section made according to plane VII-VII of FIG. 4.
Figure 8:
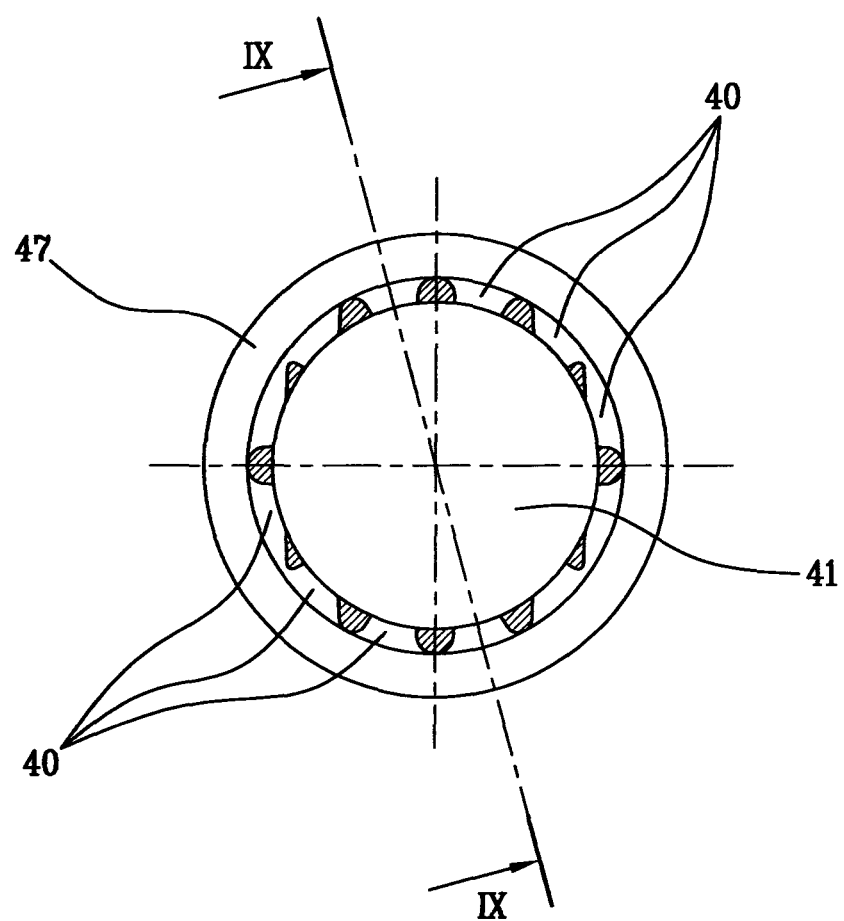
FIG. 8 is a section made according to plane VIII-VIII of FIG. 4.
Figure 9:
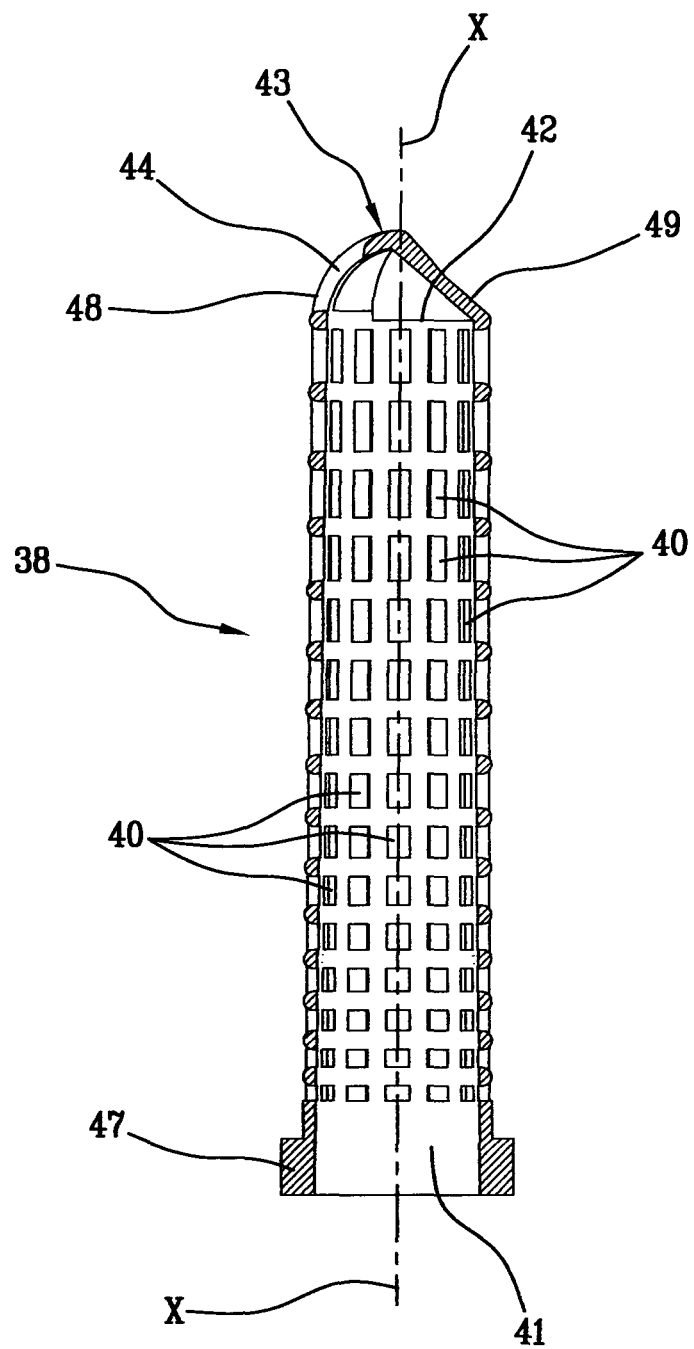
FIG. 9 is a section made according to plane IX-IX of FIG. 8.
Figure 10:
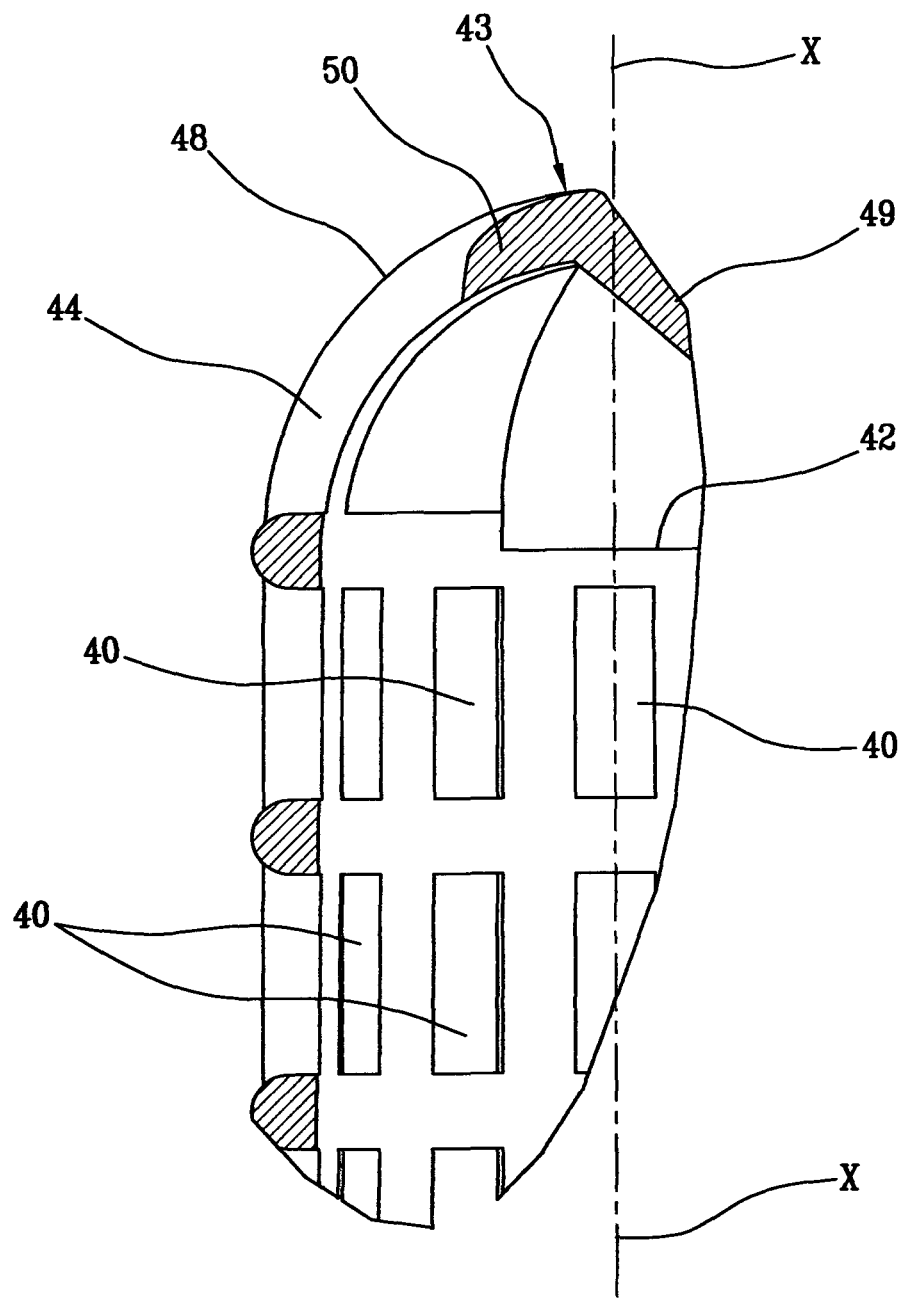
FIG. 10 is a detail in enlarged scale of FIG. 9.
Figure 11:
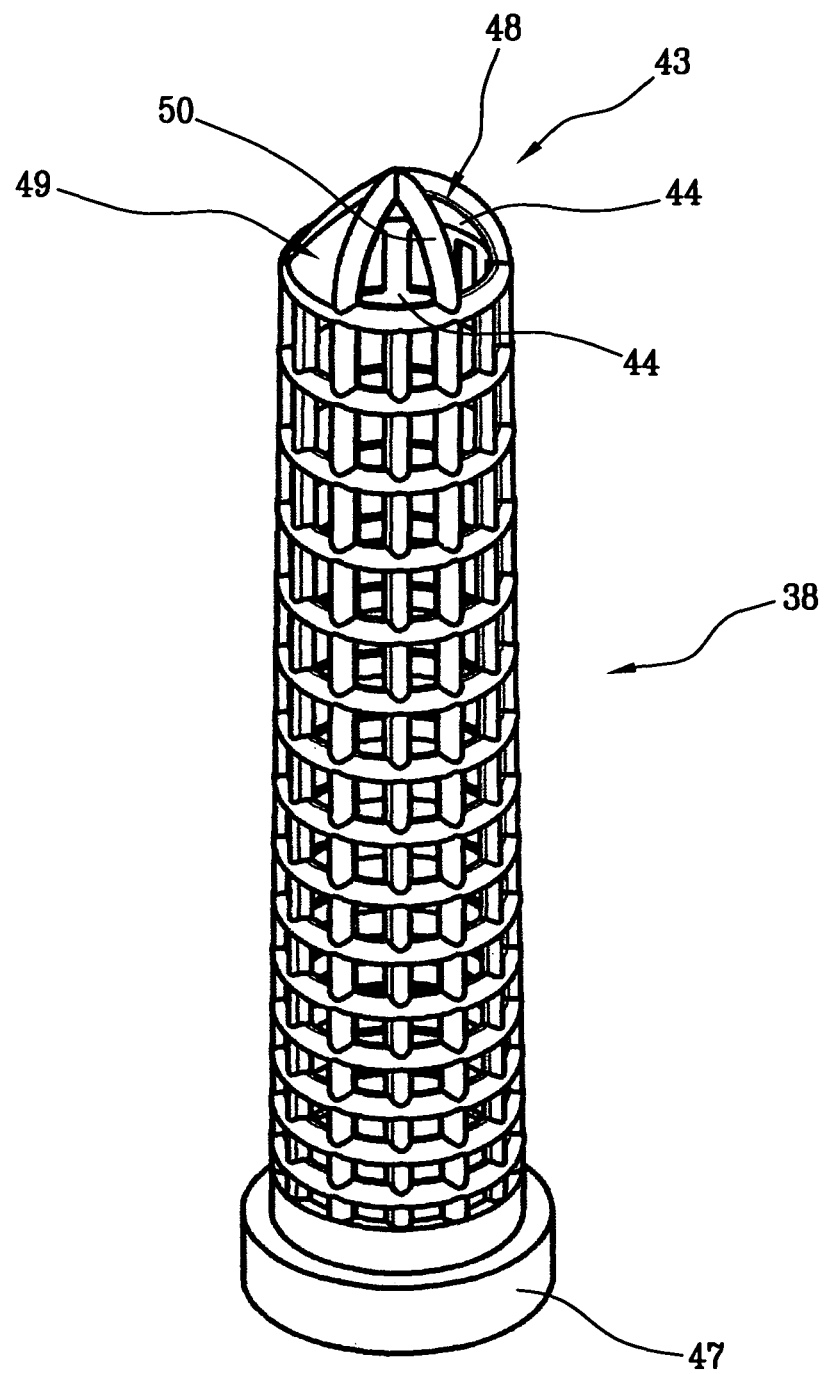
FIGS. 11 and 12 are two views, according to two different perspectives, of the filter 38 of the preceding figures.
Figure 12:
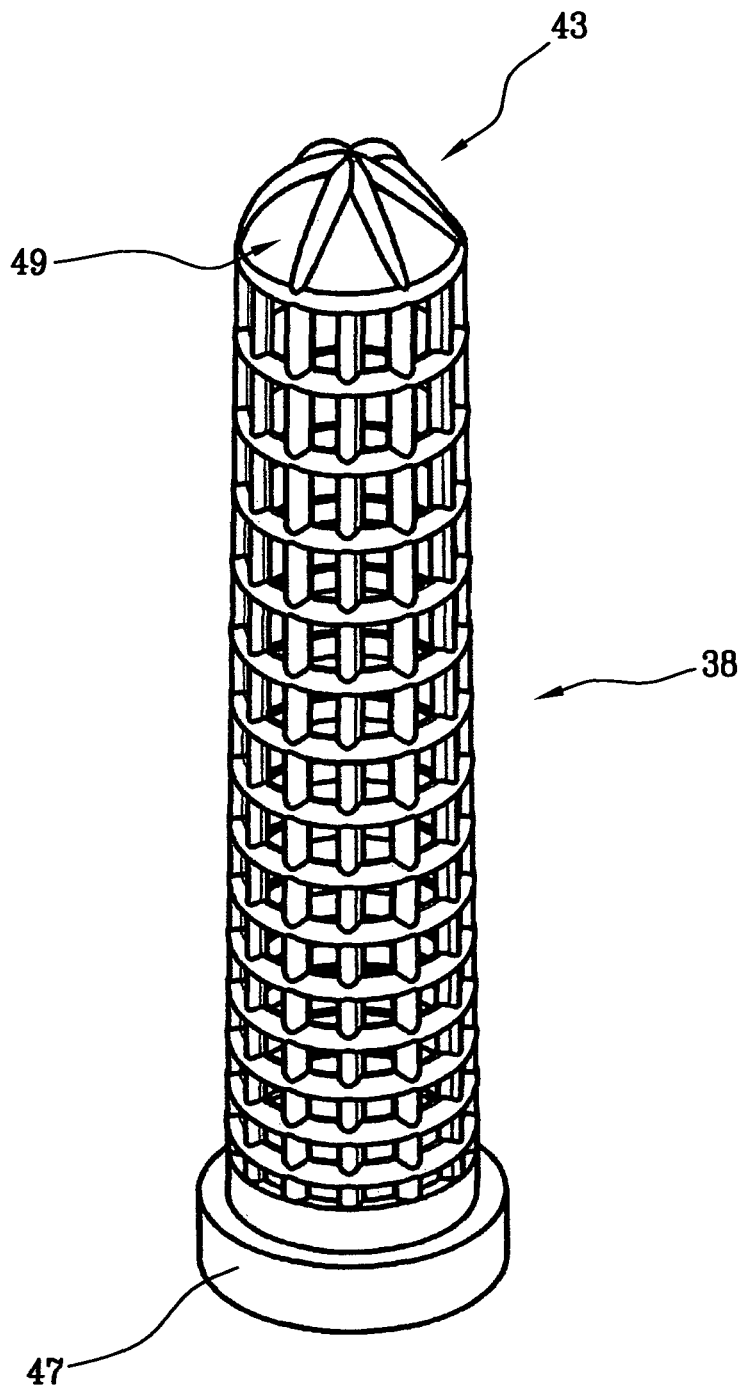

The top head 43 comprises a first portion 48 and a second portion 49 which are separated by an imaginary plane y-y passing through the longitudinal axis x-x (see FIGS. 5 and 6). The upper openings 44 are afforded on the first portion 48. At least two upper openings are afforded on the first portion 48. The first portion 48 comprises at least a rib 50 which defines the two upper openings 44. The second portion 49 has an internal surface which is semi-dome shaped. The internal surface is substantially smooth and free of irregularities, such as projections or recesses which can retain or facilitate retention of any air bubbles present internally of the top head 43. The internal surface is inclined upwards such that an air bubble in contact with or close to the surface can slide on the surface in an upwards direction and thus be directed towards one of the upper openings 44.

The second portion 49 comprises a wall realised such as not to enable passage of gas or liquids. The wall also does not allow absorption or filtration of gases or liquids. The second portion 49 is impermeable to fluids.

The first blood inlet port 35 is arranged on a first side of the expansion chamber 14. The upper openings 44 is arranged on a first side of the top head 43. The first portion 48 includes the first side. The first side may face or may be at least partly facing the above-mentioned first side of the expansion chamber 14.

The expansion chamber 14 has a lower part ("lower" being intended with reference to the use configuration) which is narrower with respect to an upper part. The first blood inlet port 35 opens into the upper part (wider) of the expansion chamber 14. The first blood inlet port 35 is, in the specific case, facing upwards, in the direction of the top 46 of the expansion chamber 14. The filter 38 is arranged in the lower part (narrower) of the expansion chamber 14. In the specific case the filter 38 is arranged closer to the first side of the expansion chamber than to the second side of the chamber, opposite the first.

The top head 43 has a second side opposite the first side. The second portion 49 includes the second side, which is formed by a fluid-impermeable wall.

The filter 38 is conformed and arranged, with respect to the pathway of the blood through the expansion chamber 14, such that the path does not substantially interest the upper openings 44 or, at most, sprays it with a flow that is prevalently directed towards the first side of the expansion chamber 14. In the specific embodiment the blood flow has an initial flow that starts from the inlet 35 and is directed towards the top 46 of the chamber, then to deviate immediately towards the second side of the chamber 14, following a curved trajectory which, at least partially, breaks against the wall of the chamber 14 defining the second side. Then the flow proceeds towards the bottom 45, broadening and slowing considerably, passing mostly through the lateral openings 40 afforded on the tubular filtering wall. The blood flow does not interest, if not minimally, the upper openings 44. In this way any solid particles present in the blood flow are effectively held back by the lateral openings 40, which are narrower (especially the lowest), while the risk of the relatively larger particles passing through the walls of the filter 38, and therefore down through the outlet 39, (which particles would theoretically be able to pass through the upper openings 44, which are relatively larger than the other filter openings) is minimised. This risk is reduced thanks to the fact that by virtue of the conformation of the filter and/or the relative arrangement thereof internally of the expansion chamber 14 and in relation to the path of the blood flow, any solid particles present in the blood flow, especially larger solid particles, cannot interest nor even pass close by the larger openings of the filter 38, i.e. the upper openings 44.

The upper openings 44 are made larger than the lateral openings 40 with the aim of facilitating the removal of any air bubbles present internally of the filter 38, especially internally of the top head 43, which, as has been found, is more subject to trapping and retaining the bubbles. The upper openings 44, being particularly large, form a preferential passage so that the air bubbles not dissolved in the blood and present in the filter 38 can freely rise upwards (preventing stalling or adhesion to the walls thereof), reaching the upper part of the expansion chamber 14, where the air separated from the blood is collected.

This ability of the upper openings 44 to leave the air bubbles free to rise towards the tope of the chamber 14 is particularly useful during the priming stage of the extracorporeal circuit, when the risk of trapping the air bubbles internally of the filter 38 can be even greater. In this case, as is known, the liquid contained internally of the expansion chamber 14 is not blood but is rather priming fluid.

In the specific embodiment described herein the top head 43 has a plurality of upper openings 44. It is however possible to provide the top head with a sole upper opening. In the specific case described herein the top head 43 has a closed part, without openings, which covers about half of the head itself, where the half-way division is defined according to a plane passing through the longitudinal axis x-x (e.g. a vertical plane if axis x-x is vertical). The closed part of the head can cover a fraction of the top head which is more or less than half thereof (for example a fraction comprised between a third and two thirds, or between a quarter and three quarters, or between a third or a quarter and a half, or between a half and two thirds or three quarters, etc.). The division into fractions is defined on the basis of (vertical or non-vertical) half-planes originating on the longitudinal axis x-x.

It is however possible for the division into fractions to be made according to other criteria. It is possible to provide an embodiment in which the asymmetric fluid passage on the top head is obtained by means of a single top opening arranged or conformed eccentrically with respect to the longitudinal axis x-x of the filter, such as for example an eccentric circular opening, or an elliptical opening or an eccentric oval opening, or a tear-drop-formed opening, or a prevalently circumferential opening, but to incomplete about the longitudinal axis x-x of the filter.

It is also possible to have various embodiments in each of which the highest point of the top head is arranged at the limit of an upper opening; or other embodiments in each of which the internal surface of the top head has, at each point of the surface, an escape route directed at least partially is upwards and towards an upper opening; or embodiments in each of which each point of the internal surface of the top head is joinable, in theory, to the zone of the expansion chamber overlying the top head via an imaginary straight line which passes through an upper opening and which has at least one upwardly-directed (vertical) component. In the above-mentioned embodiments the top head is conformed such as to prevent, internally thereof, formation of collection zones for air bubbles, such as for example niches or undercuts or concave surfaces facing downwards and lacking an upwards-directed escape route externally of the top head.

The invention claimed is:

1. An extracorporeal blood circuit, comprising:
an expansion chamber having a first port for inlet of blood and a second port for outlet of blood;
a first blood transport line having a first tract connected to the first port and a second tract connected to the second port;
a filter arranged internally of the expansion chamber, the filter comprising a tubular filtering wall configured to retain solid small bodies in a blood flow which flows from the first port to the second port; the tubular filtering wall being provided with a plurality of lateral openings; the tubular filtering wall having a longitudinal central axis; at least a part of the longitudinal central axis of the tubular filtering wall extending vertically or obliquely, with reference to a use configuration of the expansion chamber; the tubular filtering wall having an open lower end communicating with the second port; the tubular filtering wall having an upper end which extends on a lie plane that is perpendicular to said longitudinal central axis; the filter comprising a top head which is inferiorly delimited by the upper end of the tubular filtering wall; the top head being provided with one or more upper openings; each of the one or more upper openings being arranged at a lower height with respect to the first blood inlet port; the one or more upper openings forming a passage for non-dissolved gas, which passage is conformed and/or arranged asymmetrically with respect to said longitudinal central axis.

2. The circuit of claim 1, wherein the tubular filtering wall is a tubular net realised by plastic moulding.

3. The circuit of claim 1, wherein the largest possible circle that can be drawn interior to each of the plurality of lateral openings is smaller than the largest possible circle that can be drawn interior to at least a first upper opening of the one or more upper openings.

4. The circuit of claim 3, wherein said at least a first upper opening of the one or more upper openings is oriented at least partly in a transversal direction with respect to the longitudinal central axis.

5. The circuit of claim 1, wherein at least one of the one or more upper openings is oriented at least partly in a transversal direction with respect to the longitudinal central axis.

6. The circuit of claim 1, wherein at least one of the one or more upper openings is oriented in a oblique direction with respect to the longitudinal central axis.

7. The circuit of claim 1, wherein the largest possible circle that can be drawn interior to each of the plurality of lateral openings is smaller than the largest possible circle that can be drawn interior to each of the one or more upper openings.

8. The circuit of claim 1, wherein the plurality of lateral openings defines a mean passage section per opening, and in which at least one of the one or more upper openings has a passage section which is larger than the mean passage section per opening.

9. The circuit of claim 8, wherein at least one of the one or more upper openings has a passage section which is at least double the mean passage section per opening.

10. The circuit of claim 8, wherein at least one of the one or more upper openings has a passage section which is larger than a passage section of anyone lateral opening.

11. The circuit of claim 1, wherein the expansion chamber has a bottom, a top, a first side arranged between the bottom and the top, and a second side opposite the first side; the first blood inlet port being arranged on the first side; the top head being arranged closer to the first side than to the second side.

12. The circuit of claim 1, wherein the tubular filtering wall is realised in a single piece by plastic moulding.

13. The circuit of claim 1, wherein the tubular filtering wall and the top head are integrated in a single piece made by plastic moulding.

14. The circuit of claim 1, wherein the top head comprises a first portion and a second portion which are divided from one another by an imaginary plane passing through the longitudinal central axis, the one or more upper openings being afforded on the first portion.

15. The circuit of claim 14, wherein at least two upper holes are afforded on the first portion, and wherein the first portion comprises at least a stiffening rib which defines the at least two upper holes.

16. The circuit of claim 14, wherein the second portion has a semidome-shaped internal surface.

17. The circuit of claim 14, wherein the second portion is impermeable to fluids.

18. The circuit of claim 1, wherein the expansion chamber has a bottom and a top, the second blood outlet port being arranged on the bottom.

19. The circuit of claim 18, wherein the first blood inlet port is arranged between the bottom and the top.

20. The circuit of claim 18, wherein the tubular filtering wall extends longitudinally between the bottom and the top.

21. The circuit of claim 18, wherein the lower end of the tubular filtering wall is solidly connected to the bottom of the expansion chamber.

22. The circuit of claim 18, wherein at least one or each of the one or more upper openings is arranged closer to the bottom than to the top.

23. The circuit of claim 18, wherein at least one or each of the one or more upper openings is arranged at a distance from the top and at a distance from the bottom, the distance thereof from the top being at least double the distance thereof from the bottom.

24. The circuit of claim 1, wherein the top head has an external surface which is conformed asymmetrically with respect to the longitudinal central axis.

25. The circuit of claim 1, wherein the upper end of the tubular filtering wall has a diameter which is smaller than a diameter of the second port.

26. The circuit of claim 1, wherein the longitudinal central axis of the tubular filtering wall is coaxial to an axis of the second port.

27. The circuit of claim 1, wherein the first blood transport line comprises at least a tract of flexible tube which is designed for blood transport.

28. The circuit of claim 1, wherein at least a part of the top head has an external surface which is dome-shaped.

29. The circuit of claim 1, wherein the tubular filtering wall has an external surface which is truncoconical or cylindrical and coaxial to the longitudinal central axis.

30. The circuit of claim 1, wherein the tubular filtering wall has an external surface which has an axialsymmetric shape about the longitudinal central axis.

31. The circuit of claim 1, wherein the first tract of the first transport line has an end which is designed for connection with a membrane device for extracorporeal blood treatment, and wherein the second tract of the first blood transport line has an end which is designed for connection with an access device to a vascular system of a patient.

32. The circuit of claim 1, wherein the tubular filtering wall has a tapered shape, tapering from the first lower end to the second upper end.

33. The circuit of claim 1, wherein the top head is conformed such as to prevent formation of zones of collection of air bubbles internally thereof.

34. The circuit of claim 33, wherein: the highest point of the top head is arranged at the limit of an upper opening; and/or each point of an internal surface of the top head has an escape route directed at least partially upwards and towards an upper opening; and/or each point of an internal surface of the top head is joinable, in theory, to a zone of the expansion chamber overlying the top head via an imaginary straight line which passes through an upper opening and which has at least one upwardly-directed component; and/or the top head is conformed such as to prevent, internally thereof, formation of niches or undercuts or concave surfaces facing downwards and lacking an upwards-directed escape route externally of the top head.

35. An extracorporeal blood treatment apparatus, comprising:
   a membrane device having a blood chamber and a fluid chamber which are separated from one another by a semipermeable membrane;
   a fluid circuit having at least a used fluid discharge circuit which connects the fluid chamber to a drainage;
   an extracorporeal blood circuit connected to the blood chamber and realised according to claim 1.

36. The apparatus of claim 35, comprising at least a fresh fluid source and at least a fresh fluid supply circuit which connects the fresh fluid source to the fluid chamber and/or to the extracorporeal blood circuit.

* * * * *

UNITED STATES PATENT AND TRADEMARK OFFICE
CERTIFICATE OF CORRECTION

PATENT NO.        : 8,500,672 B2                                           Page 1 of 1
APPLICATION NO. : 12/745454
DATED             : August 6, 2013
INVENTOR(S)       : Caleffi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 306 days.

Signed and Sealed this

Fifteenth Day of September, 2015

Michelle K. Lee
*Director of the United States Patent and Trademark Office*